United States Patent [19]

Abe et al.

[11] Patent Number: 5,258,310
[45] Date of Patent: Nov. 2, 1993

[54] METHOD OF DIAGNOSING AGED DEGRADATION OF OIL-FILLED ELECTRICAL EQUIPMENTS

[75] Inventors: Keiichi Abe, Kasugai; Tokihiro Umemura, Mie, both of Japan

[73] Assignee: Kabushiki Kaisha Toshiba, Kawasaki, Japan

[21] Appl. No.: 692,663

[22] Filed: Apr. 29, 1991

[30] Foreign Application Priority Data

May 2, 1990 [JP] Japan ................................ 2-116482
Oct. 4, 1990 [JP] Japan ................................ 2-268190

[51] Int. Cl.$^5$ ............................................. G01N 33/30
[52] U.S. Cl. ................................... 436/60; 436/175; 73/19.11; 73/53.05
[58] Field of Search ................... 436/60, 61, 175; 204/1 T; 73/64, 19.11; 422/94-98

[56] References Cited

U.S. PATENT DOCUMENTS

| | | | |
|---|---|---|---|
| 4,410,632 | 10/1983 | Dilley et al. | 436/20 |
| 4,477,572 | 10/1984 | Azenberger | 436/6 |
| 4,744,870 | 5/1988 | Kauffman | 204/1 T |
| 4,764,344 | 8/1988 | Knab | 422/89 |

OTHER PUBLICATIONS

Bolster, R. N. et al. "Electronic Detection of Synthetic Lubricant Oxidative Breakdown", J. of ASLE Transactions, vol. 29, 3, pp. 377-382, 1986.

"Quantification of degradation products in a transformer insulation oil by a hot wire semiconductor type sensor," Takahiro Yamashita et al., National Conference of Society of Electricity, 1989, pp. 7-46.

"Handy type total combustible gas quantification device," Hideo Shinohara et al., National Conference of Society of Electricity, 1989, pp. 7-55.

*Primary Examiner*—James C. Housel
*Assistant Examiner*—David Redding
*Attorney, Agent, or Firm*—Limbach & Limbach

[57] ABSTRACT

In a method of diagnosing aged degradation of an oil-filled electrical equipment such as oil-filled power transformers, an amount of organic compounds, other than a combustible gas, dissolved in an insulation oil employed in the equipment is detected. The degree of aged degradation of the equipment is determined based on a result of detection of the amount of organic compounds.

5 Claims, 9 Drawing Sheets

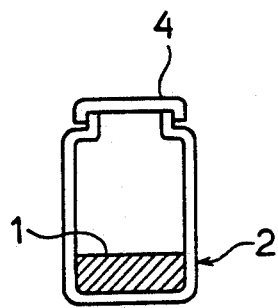 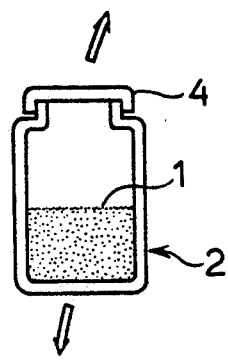 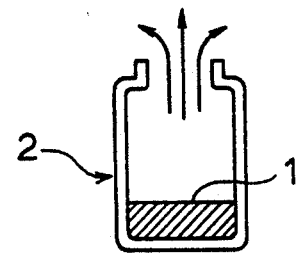
FIG.2.(a)   FIG.2(b)   FIG.2(c)
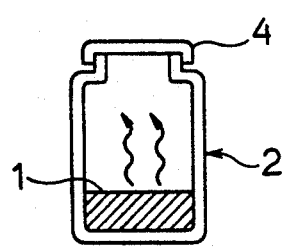 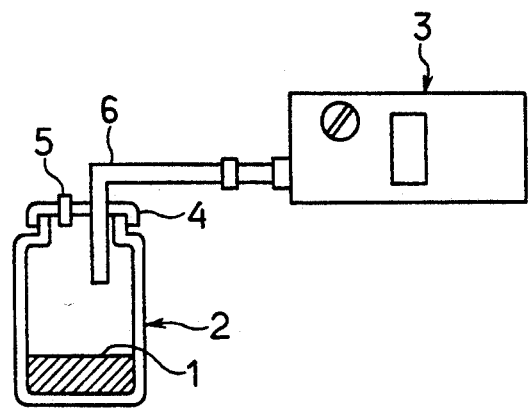
FIG.2(d)   FIG.2(e)

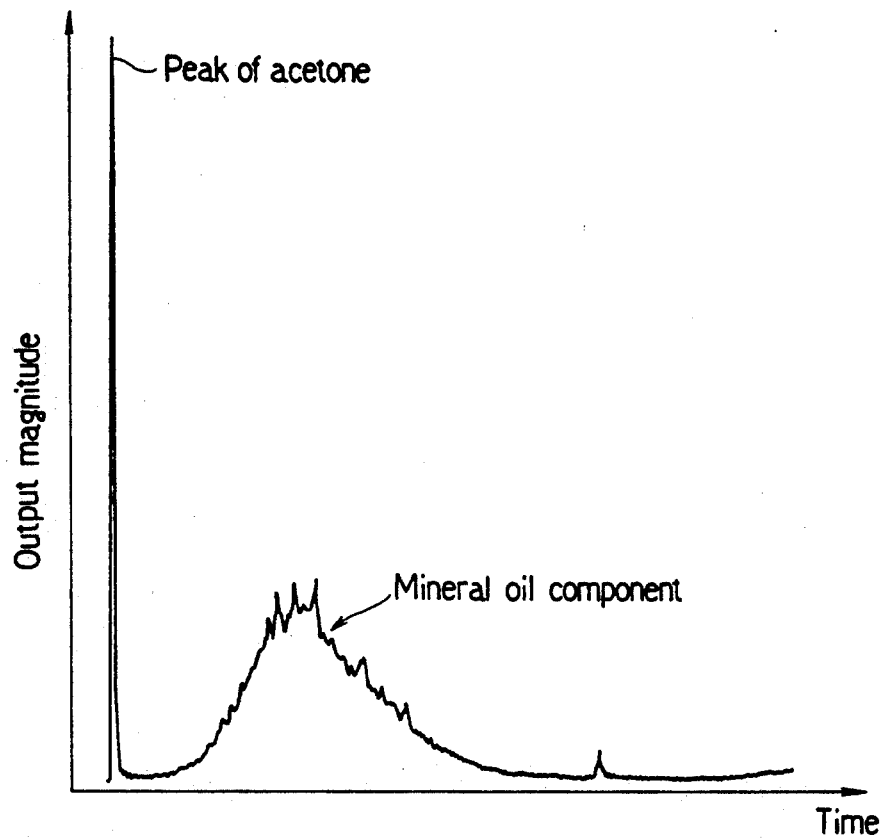
FIG.9 (a) With insulating paper
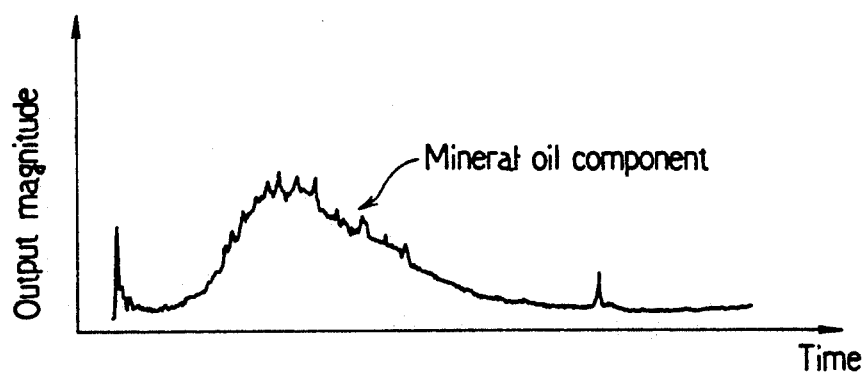
FIG.9 (b) Without insulating paper

METHOD OF DIAGNOSING AGED DEGRADATION OF OIL-FILLED ELECTRICAL EQUIPMENTS

BACKGROUND OF THE INVENTION

This invention relates to a method of diagnosing aged degradation of oil-filled electrical equipments applied to determine degree of aged degradation of oil-immersed insulators employed in oil-filled transformers, oil-filled reactors and the like.

Recently, a mere short-period power failure can cause a great deal of damage in the circumstances in which oil-filled electrical equipments such as oil-filled transformers and oil-filled reactors are used. If an accident should happen to the oil-filled electrical equipment in these circumstances, an influence of the accident could become great. Accordingly, in order that such an accident is prevented from occurring to maintain a reliable operation, reliability of equipments and installations needs to be evaluated to apply to the maintenance of the equipments and installations and the diagnosis of the equipments and installations needs to be periodically executed with respect to the degradation of the insulation performance so that the result of the diagnosis is applied to the maintenance of the equipments and installations.

In the case of the oil-filled electrical equipments, the aged degradation of oil-immersed insulators has been conventionally diagnosed in the following method. A high polymer insulation material such as an insulating paper or press board is employed inside the oil-filled electrical equipments. A combustible gas such as CO, $CH_4$, $C_2H_2$ and $C_2H_4$ or various kinds of cracked gases such as organic acid are produced with degradation of the insulation material and dissolved in the insulation oil. For the purpose of diagnosing the equipments, the insulation oil is sampled and analyzed. A total amount of CO and $CO_2$ is measured and the diagnosis of the aged degradation is performed based on the result of measurement.

However, the measurement of the amount of CO and $CO_2$ has conventionally been relied upon a method of detail analysis of gas dissolved in the insulation oil with a gas chromatograph. Accordingly, the measurement of the gas amount cannot be performed with ease since this method takes much time per measurement and a measuring facility is insufficient where the oil-filled electrical equipments are installed. Consequently, even when a large number of oil-filled electrical equipments need to be diagnosed at a time, the measurement of the total gas amount has to be performed for every one of the equipments, which takes much time. Thus, it is difficult to shorten intervals of the periodical total gas amount. Furthermore, the CO gas is also produced in the occurrence of localized heating or electric discharge in the interior of the equipment as well as by the aged degradation of the oil-immersed insulator. The occurrence of such internal localized heating or electric discharge can cause errors in the measurement of the total amount of gas produced with the aged degradation. Detail information is necessitated about an amount of oil-immersed insulator used in the equipment in order that this error factor is eliminated. An accurate diagnosis cannot be performed when such information cannot be obtained. Thus, an easy method of diagnosing the aged degradation or determining abnormality of the oil-filled electrical equipments has been desired.

SUMMARY OF THE INVENTION

Therefore, an object of the present invention is to provide a method of diagnosing aged degradation of oil-filled electrical equipments wherein an amount of organic compounds can be measured in the condition of reduced error factors and an operator can readily perform the diagnosis in accordance with the method.

The present invention provides a method of diagnosing aged degradation of insulation oil-filled electrical equipment comprising the steps of sampling, into a receptacle, a predetermined amount of an insulation oil from the insulation oil-filled electrical equipment, agitating the insulation oil contained in the receptacle for the purpose of removing a combustible gas dissolved in the insulation oil, gasifying in the receptacle organic compounds dissolved in the insulation oil after the combustible gas has been removed from the insulation oil, measuring an amount of the gas-phase organic compounds by means of a semiconductor gas sensor, and determining a degree of aged degradation of the equipment based on a result of detection of the amount of organic compounds.

In accordance with the above-described method, the combustible gas produced by the internal localized heating or electric discharge in the equipment is eliminated from a detected object. Consequently, the reliability of the aged degradation diagnosis for the oil-filled equipments can be improved.

It is preferable that the step of detecting the organic compound amount in the above-describe method comprise a process of sampling a predetermined amount of the insulation oil employed in the equipment and degassing the combustible gas from the sampled oil and a process of gasifying the organic compounds dissolved in the sampled oil and sensing gaseous substances by a semiconductor type gas sensor.

It is also preferable that the degree of aged degradation of the oil-immersed insulator be determined based on the result of detection of the organic compound amount and the determined degree of aged degradation of the oil-immersed insulator is compared with a standard degree of aged degradation converted to a period of service of the oil-filled electrical equipment to determine whether or not the equipment is in a normal condition.

BRIEF DESCRIPTION OF THE DRAWINGS

FIGS. 2(a) to 2(e) are schematic illustrations for explaining a procedure for measuring an amount of organic compound gas contained in a sampled insulation oil;

FIGS. 9(a) and 9(b) are graphs showing the results of component analysis of a gas detected from the insulation oil with and without use of the insulating paper, respectively;

DESCRIPTION OF THE PREFERRED EMBODIMENT

The following is a description of an embodiment in which the present invention is applied to diagnosis of degree of aged degradation of an oil-filled transformer.

Figure 1:
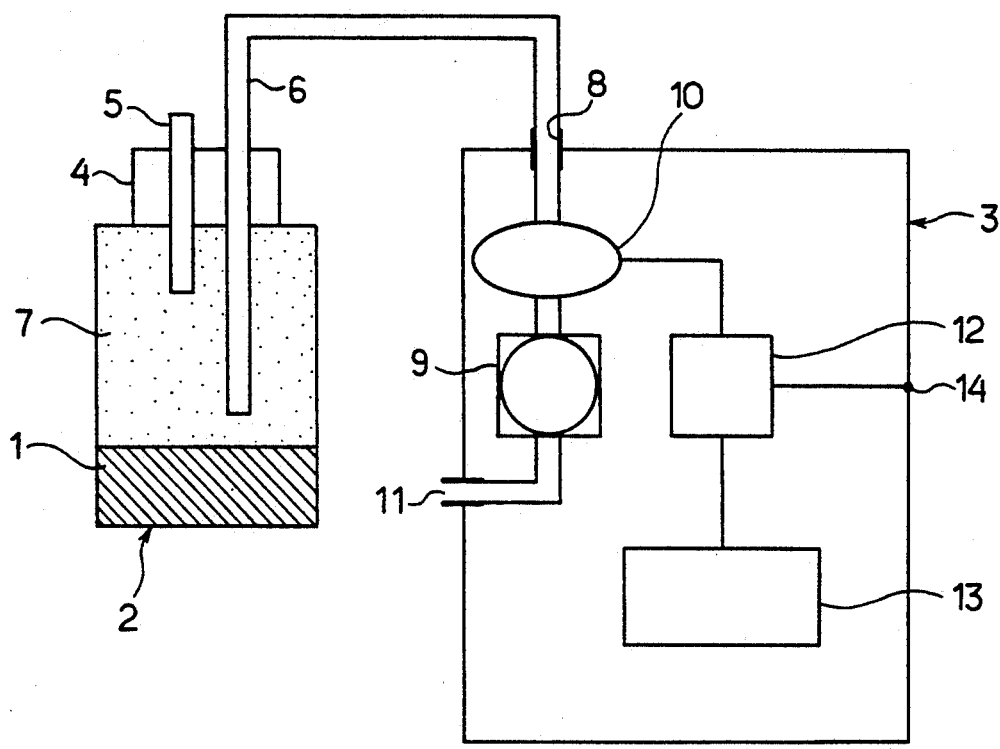
FIG. 1 is a schematic illustration of a diagnosis system arrangement in accordance with the method of an embodiment of the invention.

Referring to FIG. 1, an insulation oil 1 sampled from the oil-filled transformer (not shown) as an oil-filled electrical equipment is contained in a measuring container 2 and is to be diagnosed by a diagnosis device 3 as will be described later. The measuring container 2 has a cover 4, an outside air conduit 5 communicating between the container interior and the outside and a gas conduit 6 so that gaseous organic compounds volatilized from the insulation oil into the container interior space is introduced to the diagnosis device 3 through the gas conduit 6. A portable type odor sensor XP-329 manufactured by New Cosmos Electric Co., Ltd., Japan is employed as the diagnosis device 3, for example. The gas conduit 6 is connected to the diagnosis device 3 through a suction port 8 so that the gaseous organic compounds are sucked by a suction pump 9 provided in the diagnosis device 3. A semiconductor type gas sensor 10 is provided across a suction path in the diagnosis device 3. The gaseous organic compounds sucked by the suction pump 9 are sensed by the semiconductor type gas sensor 10, passing through the pump 9 to be exhausted from an exhaust port 11. The semiconductor type gas sensor 10 is obtained by reforming a sintered stannic oxide gas sensor so that it is sensitive to organic acids, alcohol and the like to generate an electrical signal. The semiconductor type gas sensor 10 is driven by a detection circuit 12 and a detection result is displayed on a display section 13 and also supplied to an external output terminal 14.

The procedure of diagnosing aged degradation of the oil-filled electrical equipment will now be described. The procedure is divided into (1) a sample pretreatment process, (2) a measurement process and (3) a data comparison process. These processes will be described and then, experimental data on which a condition in each process is based will be described.

(1) a sample pretreatment process (a) A predetermined amount of the insulation oil 1 (20 cc, for example) is sampled from the oil-filled transformer to be diagnosed. The sampled insulation oil is contained in the measuring container 2 (capacity of 100 cc, for example) previously cleaned with a test insulating oil. See FIG. 2(a).

(b) The measuring container 2 is closed by the cover 4 for the purpose of degassing and shaken strong, for example for five seconds so that the content is agitated. See FIG. 2(b). Consequently, a volatile combustible gas dissolved in the insulating oil is separated therefrom to reside in an interior space of the container 2. The density of the combustible gas depends upon its amount dissolved in the insulating oil.

(c) The cover 4 is detached from the container 2 and then, the container 2 is left for three minutes, for example. See FIG. 2(c). Consequently, the combustible gas such as $H_2$ is caused to diffuse from the container 2 into an atmosphere (degassing).

(d) The container 2 is again closed by the cover 4 and then, the container 2 is left for five minutes. See FIG. 2(d). Consequently, gaseous components of the organic compounds dissolved in the degassed insulation oil 1 resides in the interior space of the container 2.

(2) a measurement process:

(a) The outside air and gas conduits 5, 6 are attached to the cover 4 of the container 2. See FIGS. 1 and 2(e).

Figure 3:
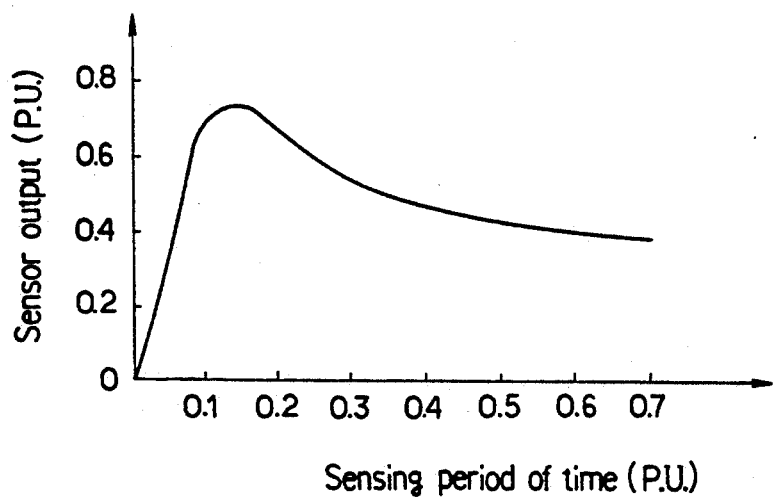
FIG. 3 is a graph illustrating a sensor output versus sensing time characteristic of a semiconductor type gas sensor.

(b) An amount of organic compounds gasified from the insulating oil is measured by the diagnosis device 3 including the semiconductor type gas sensor 10 as follows. The gas residing in the container interior space is sucked into the diagnosis device 3 through the gas conduit 6 by the suction pump 9 so that the amount of organic compound contained in the sucked gas is detected by the semiconductor type gas sensor 10. In this case, the detection output of the semiconductor type gas sensor 10 is increased with lapse of a detecting period of time and is gradually decreased after reaching a peak value, as is shown in FIG. 3. The detection circuit 12 operates to supply the peak value as measurement data to the display section 13 and the external output terminal 14.

(3) a comparison process:

The detection output of the semiconductor type gas sensor 10 obtained as described above will be caused to correspond to the number of years of use of the oil-filled electrical equipment. In this case, the actual period of operation of the equipment obtained by multiplying the number of years of use by an average load factor is used as the number of years of use in consideration of the average load factor of the equipment.

Figure 4:
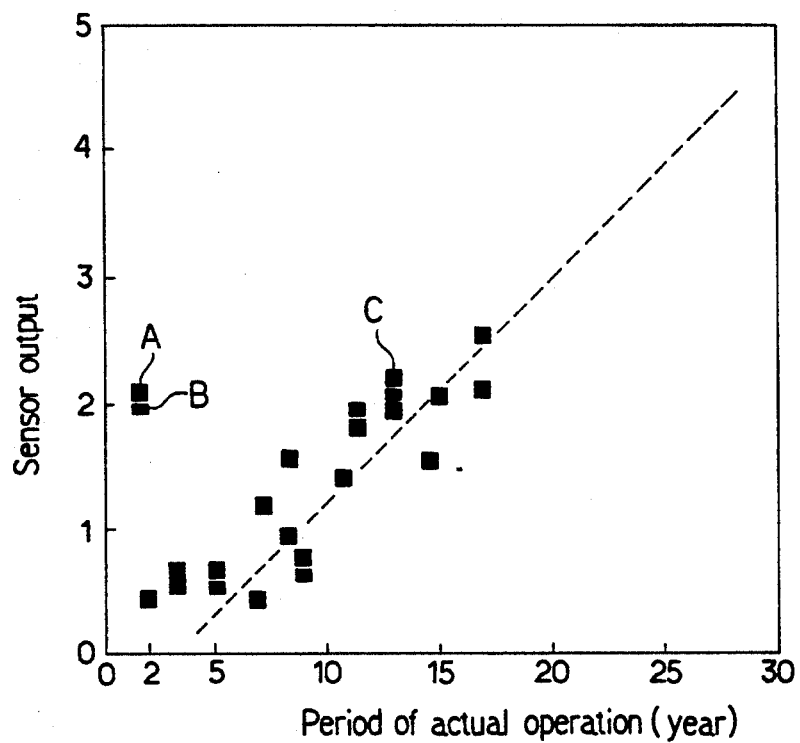
FIG. 4 is a graph illustrating results obtained by measuring degree of degradation of the oil-immersed insulators of various transformers, the results being converted to a period of actual operation.

FIG. 4 illustrates the results of measurement obtained by measuring the amount of gaseous organic compounds with respect to a number of oil-filled transformers. In FIG. 4, square and rectangular spots denote respective transformers, the axis of abscissas the period of actual operation which means the period in which the oil-filled transformer is in operation and the axis of ordinates the output of the semiconductor type gas sensor 10. From distribution of the spots in FIG. 4, it is understood that an interrelation such as shown by the broken line can be found between the sensor output and the actual period of operation. The service life of the oil-immersed insulator of the oil-filled electrical equipment corresponds to a period from the service initiation to when the retention of an average degree of polymerization of the insulator reaches 50% of the initial value in accordance with a criterion of the immersed insulator degradation diagnosis. It has been confirmed from data that the actual period of operation is 30 years. Accordingly, in the transformers in FIG. 4, they have been in normal operation for about 30 years and the output level of the semiconductor type gas sensor 10 ranges "4" to "5."

Figure 5:
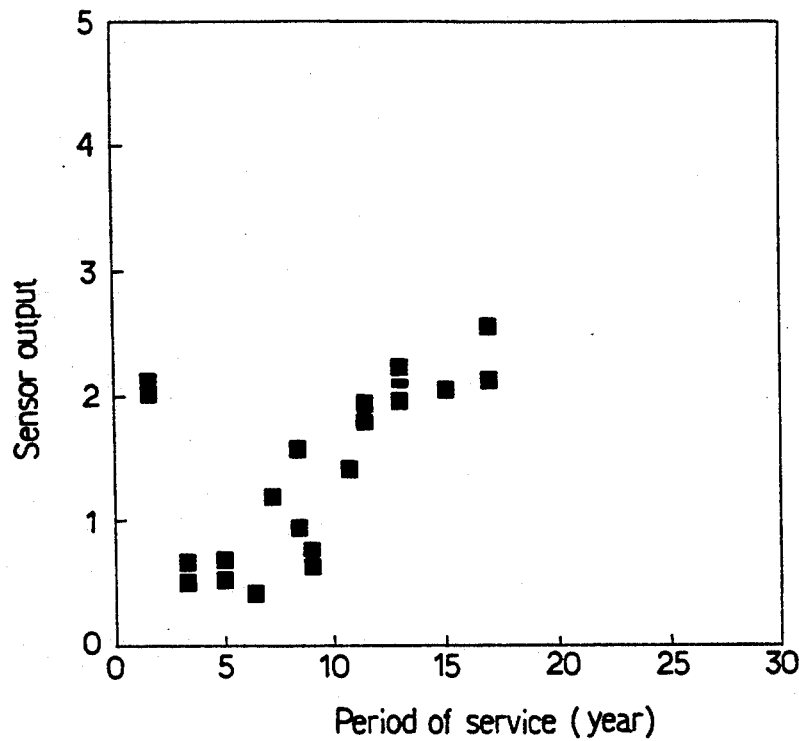
FIG. 5 is a graph similar to FIG. 4 illustrating the measurement results converted to a period of service.
Figure 6:
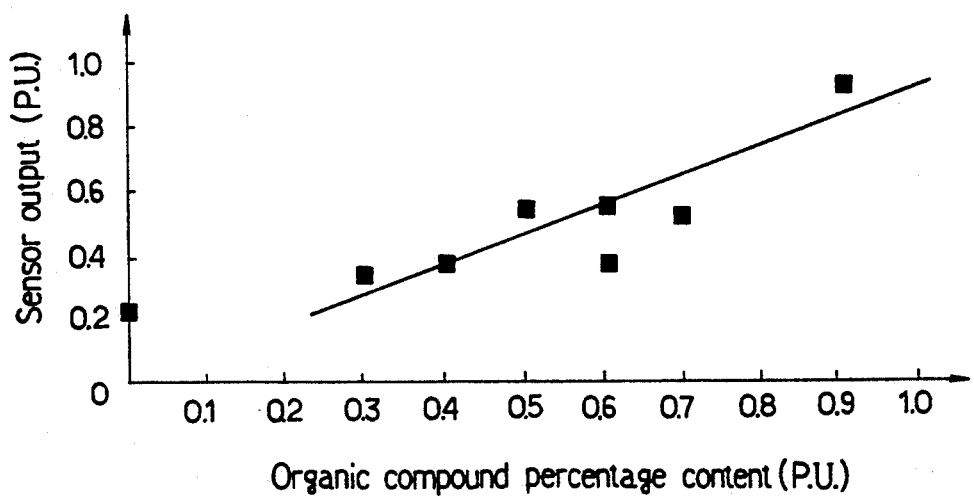
FIG. 6 is a graph showing a sensor output versus organic compound percentage content.
Figure 7:
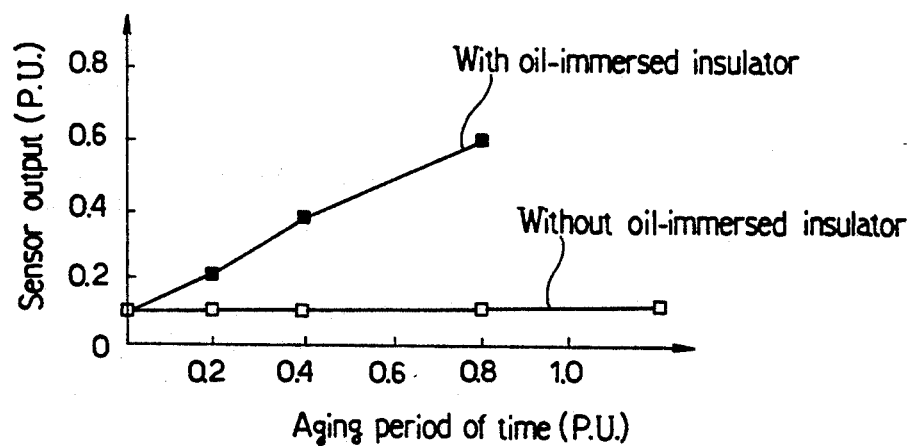
FIG. 7 is a graph showing sensor output versus aging time characteristics.

FIG. 5 shows a comparison of the output of the sensor 10 with the period of service of the oil-filled equipment, which period meaning the lapse of time from the installation of the oil-filled equipment. In this case, the factor indicative of the interrelation takes a value smaller than in the case of FIG. 4 but the substantially same interrelation can be obtained in FIG. 5 as in FIG. 4. The inventors sampled the insulation oil from various oil-filled equipments and measured the amount of organic compounds both with the above-described method and the conventional gas chromatograph in order to confirm that the detection data obtained by the sensor 10 is indicative of the substantially accurate values of the amount of organic compounds in the sampled gas. FIG. 6 shows the results of the measurement in both methods. The axis of ordinates is the output of the semiconductor type gas sensor 10 and the axis of abscissas the amount of organic compounds measured by the gas chromatograph. An interrelation represented by a solid line in the graph can be found between the sensor output and the amount of organic compounds. FIG. 7 shows interrelations between the amount of organic compounds measured with the above-described method and an aging period of time in both cases where the insulation oil with the insulator immersed therein is sampled and aged with application of heat thereto and where the insulation oil without any insulator immersed is sampled and aged with application of heat thereto. From FIG. 7, it is understood that the organic compounds are produced with aged degradation of the oil-immersed insulator.

Figure 8:
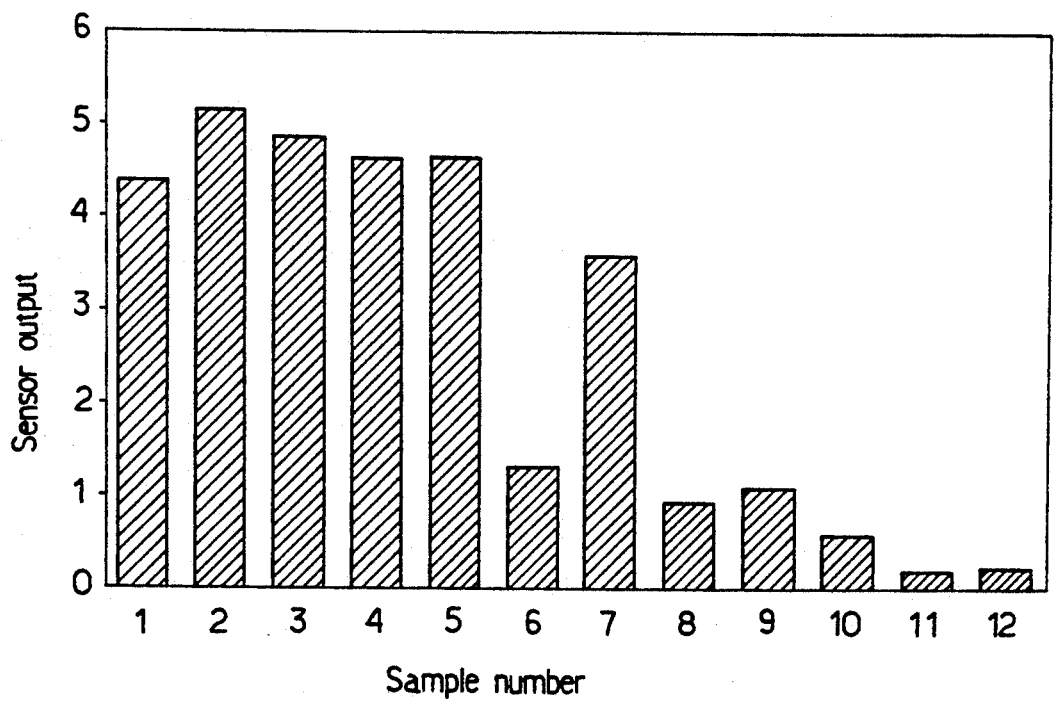
FIG. 8 is a graph showing sensitivity characteristics of the semiconductor type gas sensor.

The inventors examined sensitivity characteristics of the semiconductor type gas sensor 10 against various organic compounds. TABLE 1 shows various organic compounds and 100 ppm of each organic compound is added to the insulation oil. Each gaseous organic compound volatilized from the insulation oil is detected by the semiconductor type gas sensor 10. FIG. 8 shows the results of the detection. From FIG. 8, it is understood that the semiconductor type gas sensor 10 has high sensitivity against some kinds of organic compounds.

TABLE 1

| Sample No. | Name | Chemical formula | Molecular weight |
|---|---|---|---|
| 1 | formaldehyde | HCHO | 30.03 |
| 2 | acetaldehyde | $CH_3CHO$ | 44.05 |
| 3 | acetone | $CH_3COCH_3$ | 58.00 |
| 4 | n-butyralddehyde | $CH_3(CH_2)CHO$ | 72.11 |
| 5 | ethyl alcohol | $CH_3CH_2OH$ | 46.10 |
| 6 | acetic acid | $CH_3COOH$ | 60.00 |
| 7 | methyl acetate | $CH_3COOCH_3$ | 74.10 |
| 8 | formic acid | HCOOH | 46.00 |
| 9 | furfural | $C_5H_4O_5$ | 96.06 |
| 10 | 2-furyl methyl ketone | $OCH:CHCH:CCOCH_3$ | 110.11 |
| 11 | 5-hydroxymethylfurfural | $OC(CHO):CHCH:CCHOH$ | 126.11 |
| 12 | 5-methylfurfural | $C_6H_6O_2$ | 110.11 |

In accordance with the above-described embodiment, a small amount of insulation oil 1 employed in the oil-filled electrical equipment is sampled to be contained in the measuring container 2. After dissipation of the combustible gas from the sampled insulation oil, the organic compounds dissolved in the insulation oil 1 are gasified. The gaseous organic compounds are sensed by the semiconductor type gas sensor 10. Thus, the organic compounds produced only as the result the aged degradation of the oil-immersed insulator are sensed and the degradation products produced by abnormal conditions such as an internal discharge are eliminated from the object of measurement. Consequently, the degree of aged degradation of the oil-filled electrical equipment can be determined more accurately than in the conventional methods Furthermore, since the small amount of insulation oil is sampled and sensed by the cost-effective and small-sized semiconductor type gas sensor 10, the degradation diagnosis can be performed readily as compared with the conventional method wherein the gas chromatograph is employed.

In transformers A and B in FIG. 4, the detection output of the semiconductor type gas sensor 10 is only at the level of 2 nevertheless the period of actual operation of each transformer is below 2 years. This is an abnormally large detection output as compared with that of the transformer C wherein the detection output is approximately at the same level but is normally degraded with time after lapse of about thirteen years of service. This difference shows that abnormality accelerating degradation of the insulator is in progress in the inside of each transformer A, B and that the service life of each transformer will be expired in a short period of time when each transformer is continuously used. More specifically, it can be determined with ease whether or not the transformer is abnormal by inspecting the interrelation between the sensor output and the period of use when the detection output of the semiconductor type gas sensor 10 is abnormally high such as in the transformer A or B. When it is determined that the transformer is abnormal, further inspection is performed to clear up the cause of abnormality. Consequently, occurrence of accidents due to the abnormality of the transformer can be prevented.

TABLE 2 shows the kinds of gases dissolved in the insulation oil and the gas density with respect to each of the transformers A, B which are in the abnormal condition and the transformer C which is normally operated. It is noted that more combustible gas is produced from each of the transformers A, B than from the transformer C because of failure in each transformer A, B.

TABLE 2

| | Gas density (ppm) | | |
|---|---|---|---|
| | Transformers | | |
| | A | B | C |
| $O_2$ | 1697 | 998 | 5240 |
| $N_2$ | 15389 | 16134 | 93563 |
| $H_2$ | 61 | 44 | 15 |
| $CH_4$ | 11 | 10 | 11 |
| $C_2H_6$ | 14 | 15 | 41 |
| $C_2H_4$ | 2 | 1 | 2 |
| $C_2H_2$ | 0 | 0 | 0 |
| CO | 168 | 213 | 28 |
| $CO_2$ | 858 | 785 | 2100 |
| TCG | 256 | 283 | 97 |
| Sensor output (P.U.) | 2.09 | 2.02 | 2.21 |
| Period of actual operation (year) | 1.6 | 1.6 | 13.0 |

The inventors made experiments to confirm that the above-described method and procedure are appropriate.

(A) Detection of the organic compounds such as ketone:

The inventors analyzed components of the gaseous organic compounds produced with aged degradation of the oil-immersed insulator (insulating paper) of the oil-filled equipment and volatilized from the insulation oil. FIG. 9(a) shows the result of the analysis FIG. 9(b) shows the result of the same analysis for the gaseous organic compounds produced in the insulation oil without oil-immersed insulator. In comparison with FIGS. 9(a) and 9(b), it is noted that FIG. 9(a) wherein the oil-immersed insulator is employed shows a relatively large peak value at the left-hand side. A detail analysis of the gas component causing the large peak value shows that it is acetone (CH₃COCH₃). It is expected that the other ketones, aldehyde or alcohol can be detected depending upon selections of the insulator or insulation oil. Measurement conditions in the cases of FIGS. 9(a) and 9(b) are as follows:

(1) sampling:
The insulation oil of 2 milliliters is contained in a 25 milliliter container in each case.

(2) sample pretreatment:
The sample is heated at 80° C. for 30 minutes in each case for promotion of volatilization.

(3) measuring method:
The measurement is performed with a gas chromatograph for the organic compounds obtained from the sampled insulation oil in a head space method in each case.

(B) Method of sample pretreatment:
The following experimental data provides conditions for stable measurement in the process including the degassing step in order that the diagnosis of aged degradation of the oil-filled electrical equipments can be performed with good reproducibility and accuracy.

(1) method of sample measurement:
Since the measurement by the semiconductor type gas sensor 10 can be performed easily, various methods of sample measurement can be employed. Experiments were carried out, particularly about some methods in which the diagnosis of aged degradation can be performed with ease and accuracy. FIGS. 11(a) to 11(e) schematically illustrate various measurement methods as follows:

(a) An amount of sampled insulation oil is 500 cc and the container containing the oil is open.

(b) An amount of sampled insulation oil is 500 cc and the container containing the oil is closed with the head space capacity 500 cc.

(c) An amount of sampled insulation oil is 20 cc and the container containing the oil is open.

(d) An amount of sampled insulation oil is 20 cc and the container containing the oil is closed with the head space capacity is 80 cc.

(e) An amount of sampled insulation oil is 1 cc and the container containing the oil is open.

(e') An amount of sampled insulation oil is 5 cc and the container containing the oil is open.

Figure 10:
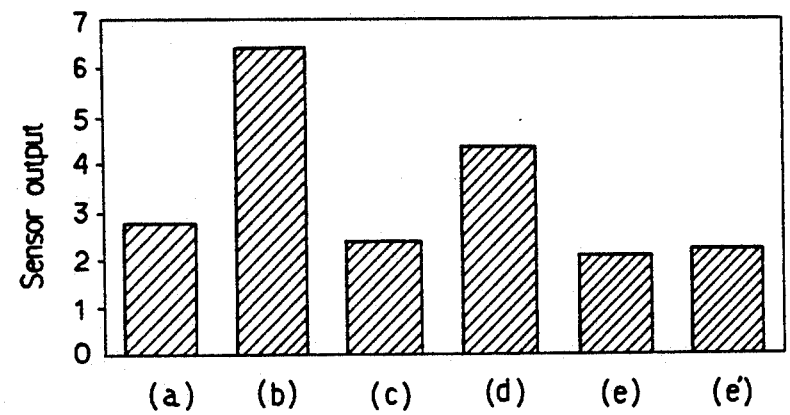
FIG. 10 is a graph showing sensitivity characteristics of the semiconductor type gas sensor in various measuring methods.
Figure 11:
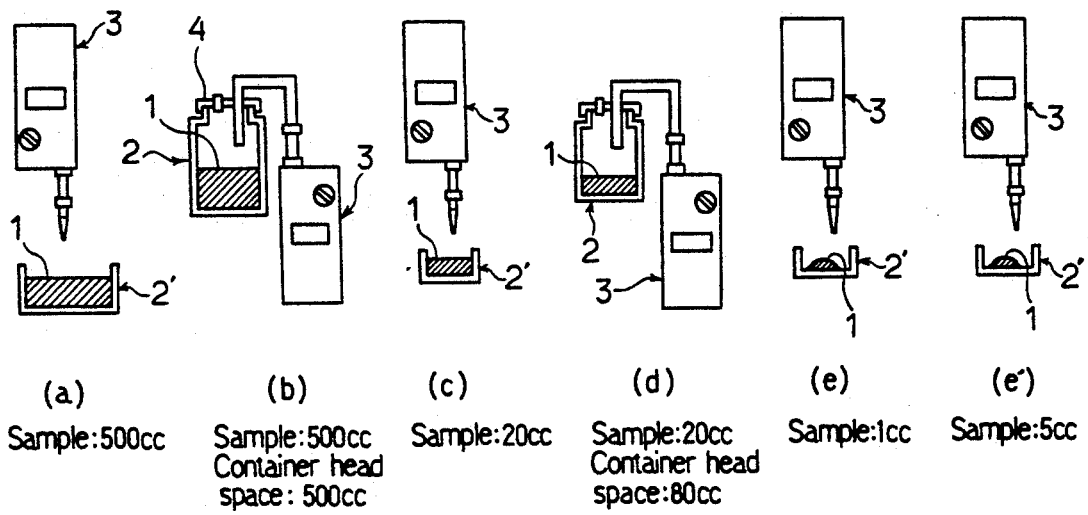
FIGS. 11(a) to 11(e) are schematic views showing measuring manners corresponding to the respective characteristics of FIG. 10.

FIG. 10 shows the sensor outputs obtained from the above-described respective methods (a) to (e'). The sensor output is obtained in each case of FIGS. 11(a), 11(c) and 11(e) in the condition that the container is open. In each case of FIGS. 11(b) and 11(d), the sensor output is obtained in the condition that the container is closed. It is understood from FIG. 10 that the sensor output level is high in the methods (b) and (d) wherein the container is closed and it is low in the methods (a), (c) and (e) wherein the container is open, irrespective of the amount of sampled oil. The sensor output is high in the method (b) in accordance with the amount of sampled oil and it is medium in the method (d). In connection with the characteristic of the semiconductor type gas sensor 10, it takes a lot of time for the sensor 10 to return to the zero point after the measurement when the high output is produced as in the method (b), while the sensor returns to the zero point in a relatively short period of time in the method (d). Each of the methods (b) and (d) is called "head space method." The method (d) is particularly advantageous in that an amount of gas volatilized from the sample is large since the head space is large relative to an amount of sample contained in the container. Consequently, since the amount of insulation oil sampled is less and the measurement efficiency is high in the method (d), it is found to be best of all the above-described methods.

Figure 12:
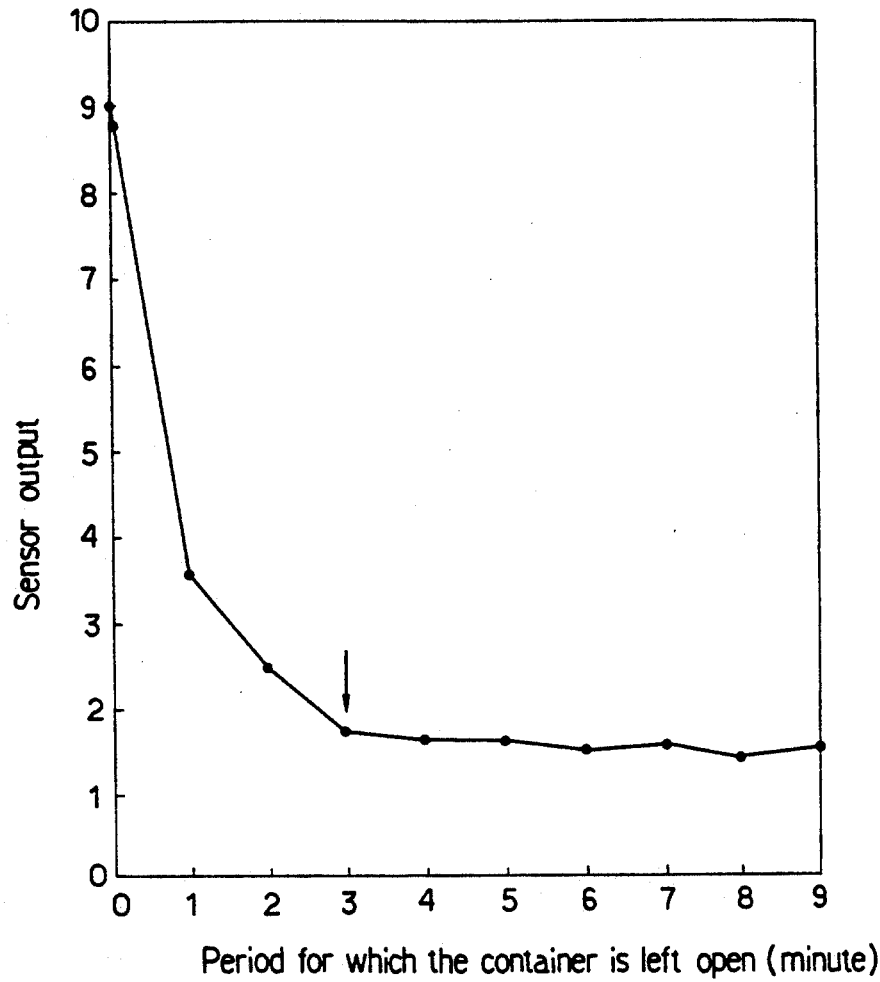
FIG. 12 is a graph showing changes in the sensor output with time in the condition that a measuring container is left opened.

(2) Sample pretreatment period of time:
An experiment was also carried out about the length of the sample pretreatment period of time. In the experiments, different periods of time were employed for the degassing step performed after shaking the container containing the sampled insulation oil. The density of residual gas in the container was measured with respect to the different periods of the degassing step. FIG. 12 shows the results of the residual gas density measurement. Additionally, an experiment was also carried out about the above-mentioned period of time for shaking the container for promotion of volatilization, under various conditions, which experiment showing that shaking the container for about five seconds is enough. From FIG. 12, it is understood that the gas filling the head space of the container finishes diffusing into the outer atmosphere after lapse of about 3 minutes in the degassing step and accordingly, the gas density in the container has been equilibrated. In this case, the amount of organic compounds was measured with the container 2 closed in the same manner as described above, as shown in FIG. 13.

Figure 13:
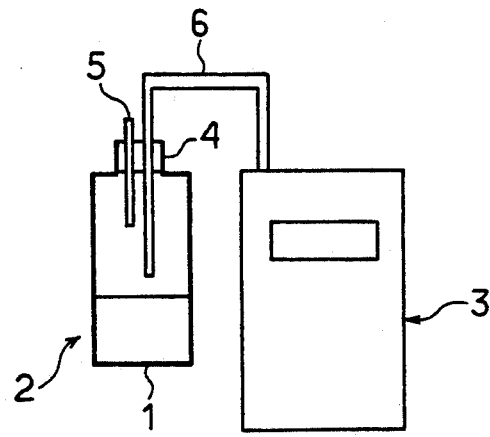
FIG. 13 illustrates an arrangement for obtaining measurement data for determination of measurement condition.
Figure 14:
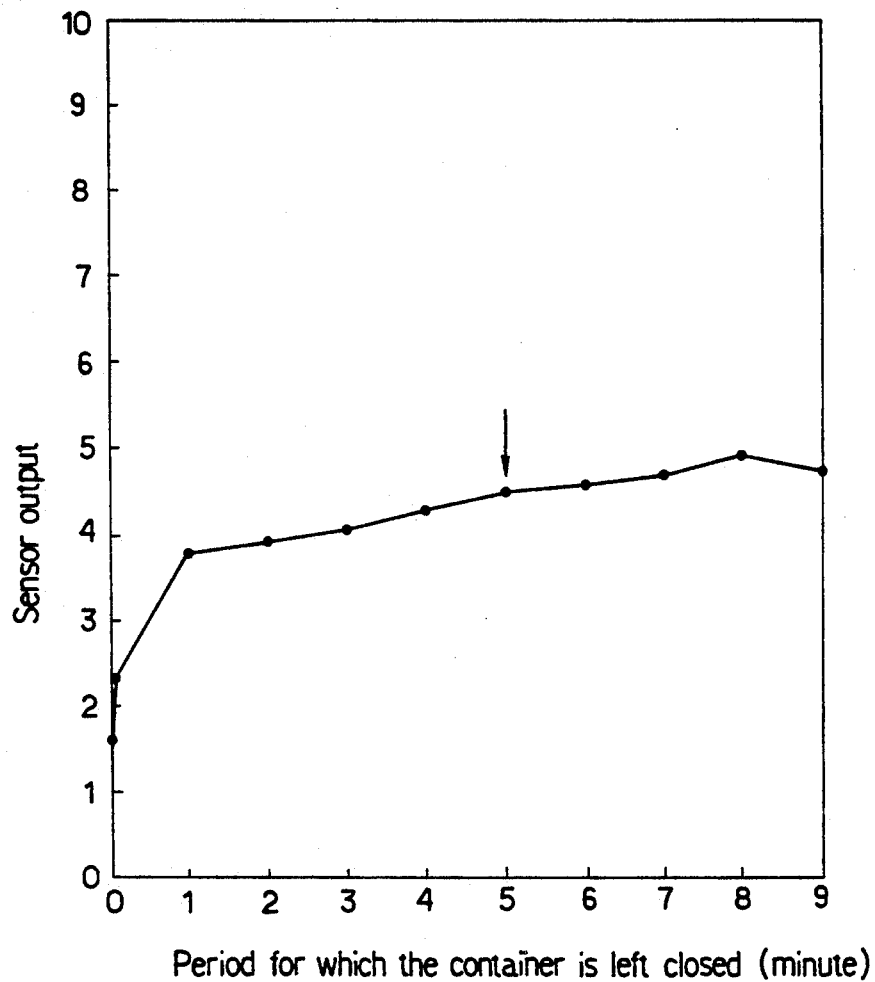
FIG. 14 is a graph similar to FIG. 12 showing the case where the measuring container is closed.

Furthermore, an experiment was carried out about the period of time for which the container is left closed so that the gas of ketone is volatilized after the degassing step. In the experiments, the amount of organic compounds was measured under the condition of different periods of time for which the container is left closed after the degassing step. FIG. 14 shows that the gas density in the container is equilibrated after lapse of about 5 minutes. In this case, too, the amount of organic compounds was measured in the same manner as shown in FIG. 13.

Based on the foregoing experimental results, the conditions for the pretreatment and measurement of the organic compounds for the aged degradation diagnosis are determined in the embodiment.

Although the above-described experimental results show advantages of the use of the semiconductor type gas sensor, the gas sensors of the other types and other method of measuring the amount of organic compounds may be employed. Fundamental methods described in the embodiment can be employed in the cases where the gas sensors of the other types are used though it can be expected that the sensor output and measurement condition will differ from those in the embodiment.

In accordance with the method of oil-filled equipment aged degradation diagnosis of the present invention, firstly, the organic compounds dissolved in the insulation oil are detected from among those produced with aged degradation of the oil-immersed insulator. Consequently, the diagnosis of the aged degradation of the oil-filled equipment can be carried out with accuracy even when an amount of insulating material used in the equipment is not clearly known.

Second, since the amount of organic compounds such as ketone, aldehyde or alcohol is detected by the gas sensor, the measurement can be performed more easily in the method of the present invention than in the conventional method in which the gas chromatograph is employed.

Third, the amount of the organic compounds such as ketone can be measured in the condition that the combustible gas has been eliminated by way of the degassing step. Consequently, the diagnosis of the aged degradation of the oil-filled equipments can be performed with further accuracy.

Fourth, the degree of degradation of the oil-immersed insulator is detected and the detected insulator degradation degree is contrasted with the period of use of the oil-filled electrical equipment so that it can be determined whether the oil-immersed insulator is normally degraded with time or degraded abnormally rapidly for the period of use of the equipment. More specifically, it can be determined with ease whether or not the oil-immersed electrical equipment is in the abnormal condition. Consequently, a detail analysis is executed for only the equipments that have been determined to be in the abnormal condition. Conventionally, however, the detail analysis need to be executed for all the oil-filled electrical equipments to be diagnosed. Thus, occurrence of accidents such as power service interruption can be prevented.

The foregoing disclosure and drawings are merely illustrative of the principles of the present invention and are not to be interpreted in a limiting sense. The only limitation is to be determined from a scope of the appended claims.

We claim:

1. A method of diagnosing aged degradation of insulation oil-filled electrical equipment, comprising the steps of:
    a) sampling, into a receptacle, a predetermined amount of an insulation oil from the insulation oil-filled electrical equipment;
    b) agitating the insulation oil contained in the receptacle for a purpose of removing a combustible gas dissolved in the insulation oil;
    c) gasifying in the receptacle organic compounds dissolved in the insulation oil after the combustible gas has been removed from the insulation oil;
    d) measuring an amount of the gas-phase organic compounds by means of a semiconductor gas sensor; and
    e) determining a degree of aged degradation of the equipment based on a result of detection of the mount of the organic compounds.

2. A method according to claim 1, wherein a gas sensor is employed in the step of detecting the organic compound amount, the gas sensor being sensitive to the organic compounds including ketone, aldehyde and alcohol to generate an electrical signal indicative of the density the organic compounds.

3. A method according to claim 1, wherein the electrical equipment comprises an oil-immersed insulator and the aged degradation of said insulator is determined by correlating the measured amount of organic compound to a value of aged degradation, which is compared with a standard degree of aged degradation converted to a period of service of the oil-filled equipment to determine whether or not the equipment is in a normal condition.

4. A method according to claim 2, wherein the degree of aged degradation is determined by correlating the measured amount of organic compound to a value of aged degradation, which is compared with a standard degree of aged degradation converted to a period of service of the oil-filled equipment to determine whether or not the equipment is in a normal condition.

5. A method according to claim 1, wherein the degree of aged degradation is determined by correlating the measured amount of organic compound to a value of aged degradation, which is compared with a standard degree of aged degradation converted to a period of service of the oil-filled equipment to determine whether or not the equipment is in a normal condition.

* * * * *